Nov. 16, 1965 M. TANTAU Plant Pat. 2,574
ROSE PLANT
Filed Aug. 19, 1964
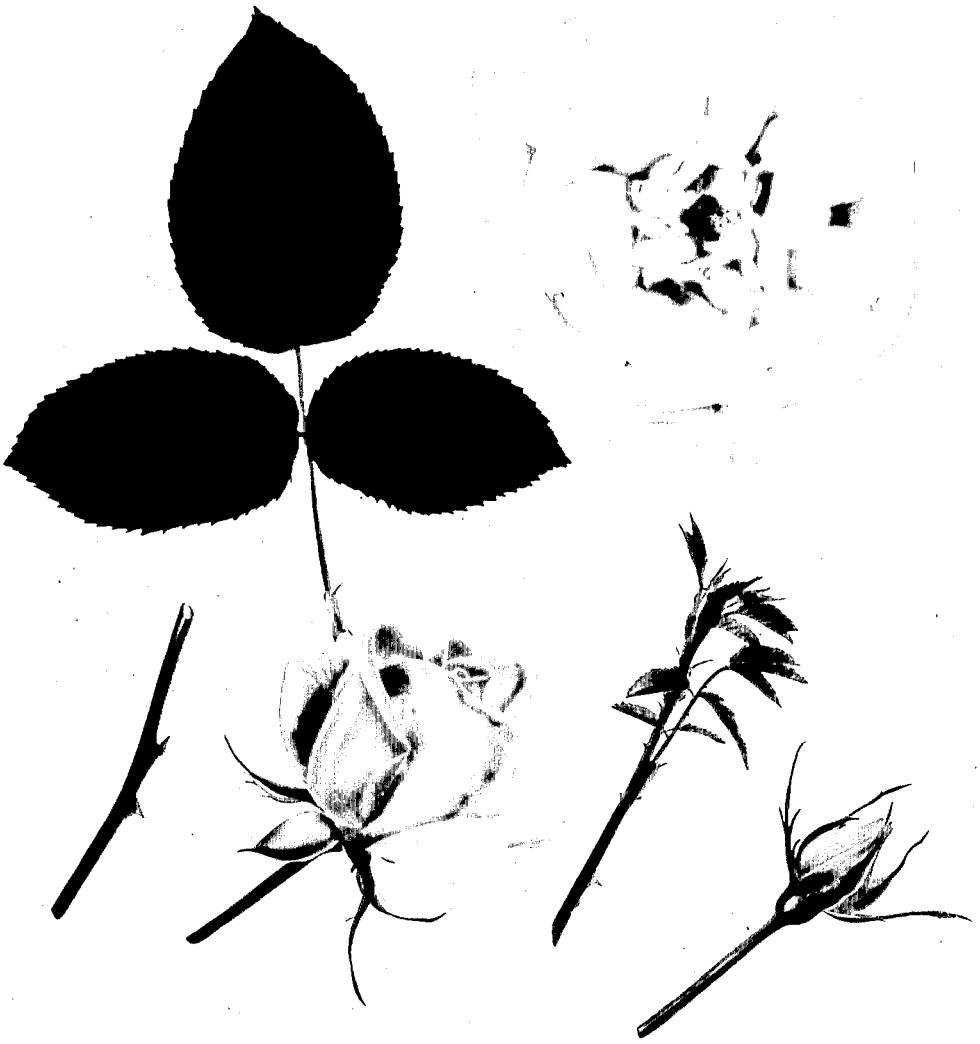
Inventor.
Mathias Tantau
By: Robb & Robb
Attorneys.

United States Patent Office

Plant Pat. 2,574
Patented Nov. 16, 1965

2,574
ROSE PLANT

Mathias Tantau, Uetersen, Holstein, Germany, assignor to Jackson & Perkins Company, Newark, N.Y., a corporation of New York Filed Aug. 19, 1964, Ser. No. 390,770
1 Claim. (Cl. Plt.—20)

The present invention relates to a new and distinct variety of rose plant of the hybrid tea class, which was originated by me by crossing the hybrid tea variety known as "Prima Ballerina" (unpatented) with the variety known as "Montezuma" (U.S. Plant Patent No. 1,383).

The primary objective of this breeding was to produce a new rose variety of the "Prima Ballerina" family, which bears flowers of a new color, while also combining with the new color the fragrance and vigor of growth that are so prominent in the parent variety "Prima Ballerina." This objective was fully achieved along with other desirable improvements, as evidenced by the following unique combination of characteristics which are outstanding in the new variety, and differentiate it from its parents as well as from all other varieties of which I am aware:

(1) A vigorous habit of growth;
(2) Freedom of bloom throughout the entire season;
(3) Large flower size and full-double flower form;
(4) A distinctive and attractive general color tonality of the flowers corresponding to Scarlet Red, lightly overcast with Rose Red, which coloring is retained from bud stage to the open flower stage; and
(5) A very strong and outstanding flower fragrance.

Asexual reproduction of the new variety by budding, as performed on my behalf at Newark, New York, U.S.A., and also at Pleasanton, California, U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Prima Ballerina."
*Pollen parent.*—"Montezuma."
Classification:
*Botanic.*—Hybrid tea.
*Commercial.*—Hybrid tea.

*Flower*

(Observations made from specimens grown in greenhouse at Newark, New York, U.S.A., in the early afternoon during the latter part of the month of May.)

Blooming habit: Recurrent—continuous.
Bud:
*Size.*—Large.
*Form.*—Ovoid; is not affected by wet or hot weather.
*Color.*—When sepals first divide—Spectrum Red, Plate 1. When petals begin to unfurl—Nopal Red, Plate 1, very lightly overcast with Carmine, Plate 1. When half-blown: inside of petals—Scarlet-Red, Plate 1; reverse of petals—Spectrum Red, Plate 1, very lightly overcast with Carmine, Plate 1.
*Sepals.*—Serrated; slightly branched; curl back when petals begin to unfurl. Color: inside—Kildare Green, Plate 31; outside—Biscay Green, Plate 17.
*Calyx.*—Color—Courge Green, Plate 17. Shape—funnel. Size—long. Aspect—smooth. Odor when rubbed—none.
*Peduncle.* — Length — long. Aspect — smooth. Strength—erect; slender. Color—Parrot Green, Plate 6.
*Opening.*—Opens up well; is not affected by adverse weather conditions.

Bloom:
*Size.*—Very large. Average size when fully expanded—from 5 inches to 5½ inches.
*Borne.*—Both singly and several together.
*Stems.*—Long; strong.
*Form (when first open).*—Cupped. Permanence—retains its form to the end, but outer petals curl back.
*Petalage.*—Double (full but open center). Number of petals under normal conditions—from 40 to 45.
*Color.*—Center of flower—Scarlet Red, Plate 1. Outer petals—Rose Red, Plate 12, lightly overcast with Scarlet Red, Plate 1. Base of petals (aiglet)—Straw Yellow, Plate 16. Inside of petals—Scarlet Red, Plate 1, lightly overcast with Rose Red, Plate 12. Reverse of petals—Rose Red, Plate 12, very lightly overcast with Tyrian Rose, Plate 12. General tonality from a distance—Scarlet Red, Plate 1, lightly overcast with Rose Red, Plate 12.
*Discoloration.*—General tonality at end of first day—Scarlet Red, Plate 1, lightly overcast with Rose Red, Plate 12. Second day—Scarlet Red, Plate 1, lightly overcast with Rose Red, Plate 12. Third day—Scarlet Red, Plate 1, overcast with Rose Red, Plate 12.

Petals:
*Texture.*—Thick; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; large.
*Persistence.*—Drop off cleanly.
*Fragrance.*—Strong. Nature—"Old Rose" perfume (centifolia).
*Lasting quality.*—On the plant—long. As cut flower—long.

*Genital organs*

Stamens, anthers: Medium; many; regularly arranged around styles. Color—Coral Red, Plate 13.
Stamens, filaments (threads): Medium length. Color—Jasper Pink, Plate 13.
Pollen: Color—Flesh Pink, Plate 13.
Styles: Bunched; medium length; thin; uneven.
Stigmas: Color—Capucine Buff, Plate 3.
Ovaries: All enclosed in calyx.
Hips: None.
Seeds: None.

*Plant*

Form: Bush.
Growth: Vigorous; upright.
Foliage: Compound of 3 to 7 leaflets.
*Size.*—Very large.
*Quantity.*—Abundant.
*Color.*—New foliage: upper side—Oil Green, Plate 5, overcast with Brazil Red, Plate 1; under side—Pompeian Red, Plate 13, with center of leaf Ecru-Olive, Plate 30. Old foliage: upper side—Varley's Green, Plate 18; under side—Light Elm Green, Plate 17.
*Shape.*—Oval pointed.
*Texture.*—Upper side—leathery and glossy. Under side—smooth.

*Ribs and veins.*—Ordinary.

*Edge.*—Serrated (saw-toothed).

*Serration.*—Both double and single; large.

*Leaf stem.*—Color—Rainette Green, Plate 31. Under side—prickly.

*Stipules.*—Medium length; bearded.

Wood:

*New wood.*—Color—Vinaceous-Russet, Plate 28. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; some hooked downward and some hooked upward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a vigorous habit of growth, freedom of bloom throughout the entire season, large flower size and full-double flower form, a distinctive and attractive general color tonality of the flowers corresponding to Scarlet Red, lightly overcast with Rose Red, which coloring is retained from bud stage to the open flower stage, and a very strong and outstanding flower fragrance.

No references cited.

ABRAHAM G. STONE, *Primary Examiner.*